US010281498B2

(12) United States Patent
Hernandez et al.

(10) Patent No.: US 10,281,498 B2
(45) Date of Patent: May 7, 2019

(54) INTENSITY MODULATED FIBER OPTIC VOLTAGE SENSORS FOR ALTERNATING CURRENT AND DIRECT CURRENT POWER SYSTEMS

(71) Applicant: Fiber Optic Sensor Systems Technology Corporation, Washington, DC (US)

(72) Inventors: Patrick Hernandez, Silver Spring, MD (US); Victor Kaybulkin, Chantilly, VA (US); Nicholas Lagakos, Silver Spring, MD (US); Christopher Vizas, Washington, DC (US)

(*) Notice: Subject to any disclaimer, the term of this patent is extended or adjusted under 35 U.S.C. 154(b) by 12 days.

(21) Appl. No.: 15/365,263

(22) Filed: Nov. 30, 2016

(65) Prior Publication Data

US 2018/0149679 A1    May 31, 2018

(51) Int. Cl.
*G01R 13/38*     (2006.01)
*G01R 13/40*     (2006.01)
*G01R 15/22*     (2006.01)
*G02B 6/36*      (2006.01)
*G01R 19/00*     (2006.01)
*G01N 24/00*     (2006.01)
*G02B 6/293*     (2006.01)
*G01N 22/00*     (2006.01)
*G01R 15/24*     (2006.01)
*G01R 31/28*     (2006.01)
*G01R 33/32*     (2006.01)

(52) U.S. Cl.
CPC .......... *G01R 15/22* (2013.01); *G01N 22/00* (2013.01); *G01N 24/008* (2013.01); *G01R 15/24* (2013.01); *G01R 19/0084* (2013.01); *G02B 6/29301* (2013.01); *G02B 6/3624* (2013.01); *G01N 2203/0641* (2013.01); *G01R 31/2822* (2013.01); *G01R 33/323* (2013.01)

(58) Field of Classification Search
CPC ............... G02B 6/29301; G01N 22/00; G01N 2203/0641; G01N 24/008; G01R 31/2822; G01R 33/323; H05H 1/46; Y10S 427/104
USPC ................ 324/72, 76.11–76.83, 96, 97, 154
See application file for complete search history.

(56) References Cited

U.S. PATENT DOCUMENTS 9,823,277 B1 * 11/2017 Lagakos ............ G01R 33/0327
2009/0252451 A1 * 10/2009 Lagakos ................ G01D 5/268
385/13

(Continued)

*Primary Examiner* — Huy Q Phan
*Assistant Examiner* — Raul J Rios Russo
(74) *Attorney, Agent, or Firm* — Hogan Lovells US LLP

(57) ABSTRACT

A fiber optic sensor for measuring voltage in direct current and alternating current systems is disclosed. The sensor may include an optical fiber probe containing transmitting and receiving fibers, fixed conductor elements, and a dynamic conductor element with a reflective surface or material. The reflector may be attached to a dynamic conductor. The two fixed conductors may be placed parallel to one another and coupled to a static voltage source. The dynamic conductor may bisect the fixed conductors and be coupled to a voltage source. The dynamic conductor may be spaced apart from the ends of the fibers in the fiber probe, and positioned so that light transmitted through the transmitting fiber is reflected by that surface into a receiving fiber. A light sensing means may be coupled to the receiving fiber, so light from a light reflected by the reflector body back into the receiving fibers is detected.

32 Claims, 3 Drawing Sheets

(56) References Cited

U.S. PATENT DOCUMENTS

| | | | | |
|---|---|---|---|---|
| 2011/0044373 A1* | 2/2011 | Lagakos | .................. | G01K 5/62 |
| | | | | 374/188 |
| 2011/0164254 A1* | 7/2011 | Ghislain | .............. | G01N 29/022 |
| | | | | 356/477 |
| 2011/0305116 A1* | 12/2011 | Lagakos | ................ | G01H 9/004 |
| | | | | 367/149 |
| 2012/0321517 A1* | 12/2012 | Ghislain | .............. | G01N 29/022 |
| | | | | 422/69 |

* cited by examiner

INTENSITY MODULATED FIBER OPTIC VOLTAGE SENSORS FOR ALTERNATING CURRENT AND DIRECT CURRENT POWER SYSTEMS

CROSS-REFERENCE TO RELATED APPLICATIONS

The theory of intensity modulated optical fiber sensors, and examples of such sensors, are disclosed in the U.S. Government-owned inventions by Nicholas Lagakos et al., described in U.S. Pat. No. 7,020,354: Intensity Modulated Fiber Optic Pressure Sensor; U.S. Pat. No. 7,379,630: Multiplexed Fiber Optic Sensor System; U.S. Pat. No. 7,646,946: Intensity Modulated Fiber Optic Strain Sensor; U.S. Pat. No. 8,195,013: Miniature Fiber Optic Temperature Sensors, and others (collectively, the "U.S. Government Patents"). U.S. Ser. No. 14/222,225, filed Mar. 21, 2014 (the "Electromagnetic Phenomena Sensor Patent Application") discloses intensity modulated fiber optic sensors that measure electromagnetic phenomena such as electrical and magnetic fields, voltage, and current. The disclosures of the U.S. Government Patents and the Electromagnetic Phenomena Sensor Patent Application are incorporated herein by reference.

FIELD OF INVENTION

This invention relates in general to fiber optic sensors for measuring voltage in alternating current and direct current systems.

BACKGROUND

In recent years, fiber optics have formed the basis for many different types of sensors, such as pressure sensors, strain sensors, and others. Optical fiber sensors can use phase, polarity or intensity modulation. Intensity modulation yields fiber optic sensors that are simpler and less expensive. The theory of intensity modulated optical fiber sensors, and examples of such sensors, are disclosed in the U.S. Government Patents by Nicholas Lagakos et al. Recently, intensity modulated optical fiber sensors have been adapted to measure electromagnetic phenomena, including electric and magnetic fields, voltage, and current, as disclosed in the Electromagnetic Phenomena Sensor Patent Application.

Electrical power monitoring and control systems require specialized sensor devices. The requirements associated with such sensors are determined by the particular monitoring and control approach employed, as well as the kind of performance expected of the monitoring or controlling system. A common type of electromagnetic sensor are instrument transformers, which measure current and voltage in a circuit when the electrical potential or current is too high to be applied directly to the measuring instruments. These transformers operate to reduce the current or voltage that is proportional to the current or voltage in the circuit, which can then be connected to measuring and control instruments. While electro-mechanical instrument transformers have been in use in electric power systems for many years, the accuracy of these devices is limited by a number of factors which impose significant measurement errors in field applications. In addition, these devices are often physically complex, are sensitive to electromagnetic interference (EMI), can be dangerous to humans in operation, and aren't physically robust.

A particular challenge in measuring voltage is associated with direct current electric power systems. Conventional measurement approaches, such as current transformers, and potential transformers physically require an alternating current in order to generate measurement, and therefore cannot provide measurement in direct current systems. An alternative approach, used to measure voltages in direct current systems, is to use a resistive voltage divider, which steps down voltage to a level where measurement is possible. However, these devices are resistive by their nature, which requires the use of coolants to avoid excessive heat generation, creates measurement drift over time as the resistor breaks down, and results in devices with relatively short useful lives. When these devices fail, they pose a safety hazard. These challenges, which become increasingly severe in high voltage applications, have led to the use of inferential approaches to the measurement of voltage of direct current systems operating at high voltages, such as transmission lines in electric networks, which results in an indirect measurement with an inherent rate of error.

A solution to this challenge is to employ measurement devices that use fiber optics for measurement. The use of fiber optics for sensors in general, and for electromagnetic measurements in particular, is an alternative that addresses the accuracy, EMI sensitivity, safety, size, and robustness concerns inherent in existing electro-mechanical electric system measurement. Since fiber optics use light rather than electricity as the basis for measurement, a fiber optic sensor is generally insensitive to EMI and is therefore more efficient in an environment that has a large amount of electromagnetic energy. As a result, fiber optic sensors can be located adjacent to or attached to circuits that generate large electro-magnetic fields without negative effects to either the measurement or the measuring equipment.

Intensity modulated fiber optic sensors are an alternative means of achieving accurate measurement of electric fields and voltage in both direct current and alternating current systems. It is an object of this invention to offer an fiber optic sensor that is: highly accurate in the measurement of direct current and alternating current power; linear in output measurement; capable of use in areas with high potential for EMI; physically robust; and physically simple.

SUMMARY OF THE INVENTION

An aspect of the invention is directed to a fiber optic sensor for measuring electromagnetic phenomena, including electrical fields and voltage, in either direct current or alternating current power systems. The embodiments of the sensor described herein use intensity modulated optical fiber sensor technology to measure these phenomena.

The described embodiments of the sensor may include an optical fiber probe including a transmitting fiber and at least one receiving fiber, a reflective surface or body that is a part of or is attached to a material that exhibits a physical displacement due to a force exerted upon the material due to an electromagnetic phenomena, here, voltage. The reflective surface may be spaced apart from the ends of the fibers and positioned so that light, transmitted through the transmitting fiber, is reflected by that surface into at least one receiving fiber. A light sensing means may be coupled to the second end of the at least one receiving fiber, so that in operation light from a light source, launched into the transmitting fiber, propagates through the fiber and emerges at the end, propagates a short distance from the end of the fiber, and is reflected at least partially by the reflector body back into the receiving fibers, the reflected light then propagates through the receiving fibers, and the light is detected by the light sensing means.

In operation of the disclosed embodiments, the physical displacement in the material is caused by a force exerted upon the material due to an electromagnetic phenomena, with embodiments that can be selected whereby the electric field or voltage of interest is isolated for measurement. The physical displacement causes a change in the distance between the fiber ends and the reflective surface of the sensor, modulating the amount of light received in the receiving fiber or fibers and detected by the light sensing means. The intensity of the light received may thereby be modulated in relation to the intensity of voltage measured.

Thus, the voltage or electric field of interest is indicated by the physical displacement of the material in response to the force, and the displacement of the material is measured by the amount of light detected by the light detecting means.

DETAILED DESCRIPTION OF THE INVENTION

Figure 1:
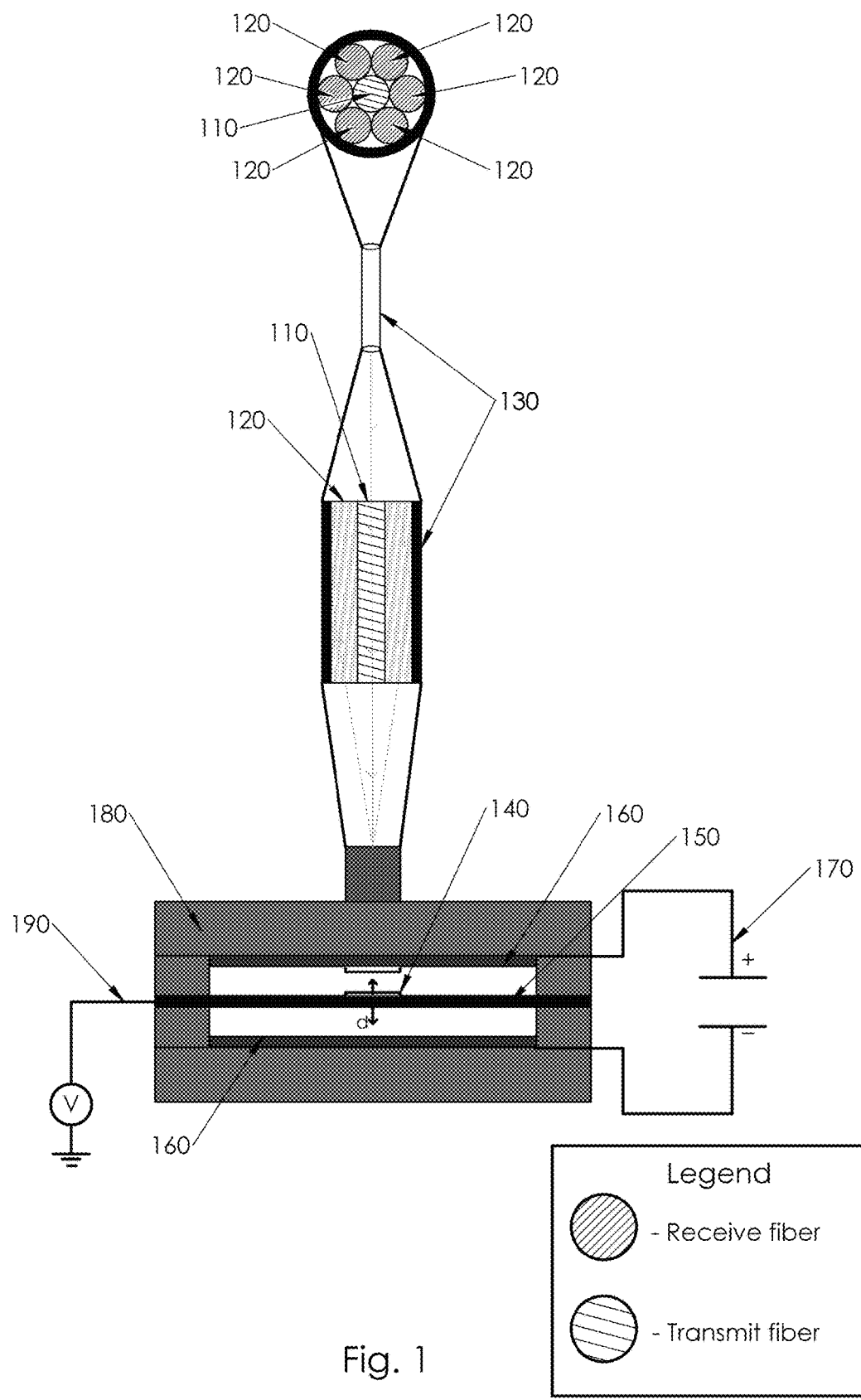
FIG. 1 shows an embodiment of a fiber optic electromagnetic phenomena sensor, configured to measure voltage or electric fields utilizing a single optical probe.

The embodiments of the fiber optic voltage sensor disclosed herein use non-interferometry based optical measurement to derive highly accurate measurements of voltage in both alternating and direct current applications, and can be used across a wide range of voltage levels.

The disclosed embodiments of the sensor may include a fiber optic probe, having a transmitting fiber for transmitting light and at least one receiving fiber for receiving light, which is placed adjacent to a reflective surface, with space between the probe end and the reflective surface. The reflective surface may be either a part of, or attached to, a material that exhibits a physical displacement in response to an electromagnetic phenomena.

The physical displacement in the disclosed sensor embodiments are produced in a material in response to the introduction of an electric field, or voltage, when the material is placed within a static electric field. The displacement in the material causes a change in the distance between the fiber optic probe and the reflective surface. The transmitting fiber is coupled to a light source and the receiving fiber or fibers are connected to a light sensing means so that, in operation, the displacement of the material causes the light transmitted through the transmitting fiber to be reflected into the receiving fibers with an intensity that is modulated in a manner proportional to the displacement experienced by the material in response to the electromagnetic phenomenon.

In a preferred embodiment, the fiber optic sensor measures the displacement in a material that is created by the force explained by Coulomb's Law, allowing for measurement of electric fields or voltage. Under Coulomb's Law, the force produced by two charged objects is proportional to product of the quantity of charges upon the objects and the distance between the objects. This force can create a displacement in a material, or, if the charged objects are held in a fixed arrangement, generates a static electric field between the objects. By introducing a third charged object between the two fixed charges (the static electric field), a force will be created upon the third charged object, which force acts to physically displace the conductor in a direction of the charge of opposite polarity and with a displacement that is proportional to the charge present in the third object (i.e.: the voltage applied to the conductor).

Coulomb's Law can be expressed as follows where a voltage source is applied to a pair of conductors where the two conductors have opposite charges:

$$F = \frac{q}{4\pi \varepsilon o\, \varepsilon r\, d}.$$
Equation 1

Where:
F=Force
q=electric charge
$4\mu\varepsilon_o$=Coulomb's constant
$\varepsilon_o$=vacuum permittivity of free space
$\varepsilon_r$=relative permittivity of medium
d=distance between the charges From the above, it can be seen that, if a voltage is applied to a conductor that is in a static electric field, the conductor will displace in a direction towards its opposite polarity and with a given force. This principle can be used to construct a sensor that isolates for the measurement of voltage by measuring the displacement caused by the force explained by Coulomb's Law. In the disclosed embodiments, the sensor is constructed to isolate for the measurement of voltage by creating a static electric field between two conductors that are arranged in a fixed configuration parallel to one another and introducing a third conductor that bisects the two fixed conductors, at an equal distance and parallel to both of the two fixed conductors (and thus subject to equal force by the static electric field generated between these two fixed conductors).

If the two conductors are held in a fixed relationship relative and parallel to one another, and a voltage is applied across the two fixed conductors, they will generate a static electric field between the conductors. The creation of the static field between the two fixed conductors can be achieved by coupling the conductors to a battery, a dry pile, a DC converter or any other known means of generating a voltage difference between the two conductors. The dimensions of the fixed conductors, and the space between them, can be set to a desired distance, and the strength of the electric field between the conductors can be pre-determined.

If the third conductive element (placed between the two fixed conductive elements) is constructed in a manner so as to permit this element to displace in response to a force, and then a voltage is applied to the third conductor, that conductor will displace in the direction of the fixed conductor that possesses the opposite polarity of the applied voltage and away from the conductor of the same polarity. The force is expressed as a linear response to the magnitude of the current, with the force being proportional to electric charge (voltage), consistent with Equation 1. The output exhibits a linear relationship between the displacement experienced by the conductive element and the voltage applied, providing the sensor with a greater dynamic range when compared to approaches in which a pair of parallel conductors are used (i.e.: a double conductor sensor) which results in a quadratic output and signal with a signal at twice the fundamental frequency of the voltage source of interest in AC applications.

The force exerted upon the third conductive element creates a physical displacement in the conductive material in a direction towards the fixed conductor that possesses the opposite polarity of the introduced voltage. The displacement of a given material in response to such a force can be determined. For example, if the voltage carrying conductive element is configured as a conductor beam that is fixed at both ends, it is known that the force exerted upon the beam will be uniform, causing the beam to displace according to the following:

$$x = \frac{5}{384} \frac{F l x^3}{EI}.$$  Equation 2

Where:
$\chi$=physical displacement of material at center
5/384=scalar constant based upon method of material constraint
F=force
l =length of wire
E=modulus of elasticity
I=moment of inertia The scalar constant of the element is a mechanical property of the conductive beam that relates the deflection of a material based upon the configuration of the material and the load (force) on that material, and is a property known for many configurations of materials. The length of the conductive beam is readily known, the modulus of the elasticity is readily available information for many materials, and the moment of inertia is a known property of a material with given characteristics. For example, a conductive wire with a circular cross section has a moment of inertia that can be expressed as $\pi d^4/64$. This displacement in the conductor produced by the force explained by Equation 1 and resulting in a displacement in the material in a manner similar to that explained by Equation 2 can be measured by the fiber optic probe.

Thus, the force explained by Coulomb's law causes physical displacement of the third conductive element carrying a voltage of a given polarity and known configuration in a given and known direction based upon the introduced voltage's polarity when such a conductor is placed within the static electric field created by the two fixed conductors. The displacement is measured by the fiber optic probe and such displacement is proportional to voltage, as explained by the principles set forth in Equation 1. As can be seen, the displacement of the third conductor would be in a uniform direction in the case of a direct current system, but would be bi-directional (i.e.—displacing in alternating directions relative to the fixed conductors) in an alternating current system with a frequency equal to the fundamental frequency of the introduced voltage source (such as 60 Hz).

FIG. 1 shows an embodiment of a fiber optic voltage sensor featuring a fiber probe and a material that exhibits a physical displacement in response to voltage, with the force creating the displacement being explained by Coulomb's Law described in Equation 1 and consistent with the above description.

A fiber bundle 130 featuring a transmitting fiber 110 having a first and second ends is placed adjacent to a reflective surface 140. The first end has a polished finish and the second end is coupled to a light source (not shown). The fiber bundle also features a multitude of receiving fibers 120 disposed around the transmitting fiber with each receiving fiber having first and second ends where the first ends are also polished and the second ends are coupled to a light detecting means (not shown). The fiber bundle is disposed within a tubing 130 such that the first end of the transmitting fiber and the first end of each receiving fiber is perpendicular and adjacent to the reflective side of the material 140 to be measured that exhibits a physical displacement when carrying a voltage and placed within a static electric field, with space between the fiber ends and the reflective side of the material. The fiber bundle is disposed within and through the conductive element such that it is positioned flush or protruding through the conductor, which sets the fiber bundle at a fixed distance (and thus the transmitting and receiving fiber ends) from the reflective surface of the conductive element.

Here, the material that will experience the displacement in response to the force that will be measured is a conductor 150 which is itself reflective (i.e.: elements 140 and 150 are the same material, here a strip of polished phosphor bronze). However, the material can have an attached reflective body or coating, layer, or other reflective means that is comprised of a reflective material such as a metal (aluminum, beryllium, chromium, copper, gold, molybdenum, nickel, platinum, rhodium, silver, tungsten, and/or an alloy of any other suitably reflective metal). In this embodiment, the conductive element 150 that exhibits a physical displacement to the introduction of a voltage is a conductive strip of phosphor bronze, but any conductive material can be used, such as copper, silver, gold, aluminum, steel, or graphene. Two other conductors 160 constructed of copper and cut into square plates are arranged in a fixed and parallel relationship to one another and are coupled to a voltage source 170, which can be generated by a battery, a dry pile, a DC voltage converter, or any other known means, in order to generate a static voltage field reference between the conductors 160. These elements can be held in the fixed relationship described using any means, but in this embodiment a ceramic housing 180 is constructed in order to maintain the fixed dimensional relationships of the various sensor elements.

The bronze strip conductor 150 is positioned such it is parallel to the two copper conductors 160 and bisecting the electric field created between them. In operation, a voltage potential, denoted "V", is introduced to the conductive element 150 through the use of a conductive wire 190. In the presence of the electric field generated between the two copper conductors 160 that are coupled to the battery or other voltage source 170, the introduction of a voltage from the voltage source of interest 190 to the conductive element 150 will cause the element to experience the force explained by Coulomb's law in a known direction depending upon the polarity of the voltage in relation to the polarity of charges on the pair of parallel copper conductors. The force will result in a displacement of the material and change the distance between the reflective surface 140 of the conductive element 150 and the fiber ends, changing the amount of light reflected into the receiving fibers and detected by the light sensing means.

As shown in FIG. 1, the force exerted upon the conductor 150 results in displacement in the wire towards the direction of the fiber optic probe, the force creating a physical displacement consistent with the displacement equation described in Equation 2. In parallel, light from the light source is launched into the transmitting fiber, propagates through the transmitting fiber, emerges at the opposite end, propagates a short distance, and is reflected by the reflective surface of the conductor into the receiving fibers, the light then propagates through the receiving fibers, and is detected by light sensing means (not shown).

The displacement in the voltage-carrying conductor due to the force explained by Equation 1 in a direction relative to the fiber probe causes a change in the amount of light reflected by the reflective surface of the conductor 150 and into the receiving fibers. The amount of displacement experienced by the conductor is proportional to the voltage flowing through the conductive element 150 from the voltage source 190. An increase or decrease in the distance between the optical fiber probe and the reflective surface will cause a change in the amount of reflected light received in the optical fiber. Thus, the intensity of the light coupled into the receiving fibers modulates in relation to the magnitude of the current that is passed through the current carrying conductor. The distance between the end of the optical fiber probe bundle and the reflective surface of the material can be set to a predetermined distance at which the sensitivity of the sensor is high and has an optimal dynamic range. The optimal probe-reflector distances are disclosed in detail in the Electromagnetic Phenomena Sensor Patent Application.

The type of fiber employed in the embodiment shown in FIG. 1 is generally an optical fiber having a core that is preferably made of glass. The cladding may be plastic or some other material. In a preferred embodiment fibers with a high numerical aperture are used. Generally fibers with a numerical aperture of >0.2 are employed. A high numerical aperture provides for greater efficiency in the coupling and transmission of light. The fiber may be a multimode fiber. Multimode fibers and fibers featuring high numerical apertures are not required, however. When employed in systems that have a great distance between the source and the reflective side of the material a fiber having a high numerical aperture is not critical.

Generally, multimode fibers with a combination of a thick core and thin clad fiber are preferred. Light incident on clad is lost, thus the core needs to be as close in proximity to the outer perimeter of the clad is possible to ensure efficient light coupling in the core. Thus, light coupling within the fiber is maximized with a thick core thin clad structure. This however, does not limit the use of fibers in this device to multimode fibers with thick core thin cladding structures. Varying degrees of effectiveness and light coupling are possible with other fiber configurations.

In a preferred embodiment, one end of the transmitting fiber has a polished finish and the opposite end of the transmitting fiber is coupled to the light source (not shown). The first ends of the receiving fiber or fibers also feature a polished finish, with the opposite ends coupled to the light sensing means (not shown). The optical fiber features a 200 µm glass core, and 230 µm plastic clad, a 500 µm Tefzel plastic coating, and a numerical aperture of approximately 0.37. The plastic coating is stripped and epoxy is applied to the fibers so the fibers form a symmetric bundle. The fiber bundle is inserted into a tubing 130 so the fiber bundle is contained within the tube, forming a probe. The fiber probe is positioned such that the first end of the transmitting fiber and the first end of each receiving fiber is adjacent to the reflective surface with space between the first fiber end and the reflective surface. A broad dynamic sensitivity maximum has been found for a probe-reflector separation between 180 and 250 µm for this embodiment, but other separations may be preferable based upon the construction of the probe (i.e. —the number of fibers utilized).

The light sensing means can be any known means of detecting light, but in this embodiment is at least one silicon PIN diode. LEDs represent an efficient way to launch light into the fiber probe. LEDs are generally low cost and feature low noise operation in a fiber system. LEDs also tend to be very stable over extended periods of time. Laser diodes may also be used, although they increase the expense and complexity of the system. Laser diodes also tend to introduce additional noise to the sensor package. Other light sources may also be used. One suitable LED for use as a light source is an Optek OPF370A LED emitting light at 850 µm wavelength.

As shown in FIG. 1, and described above, a preferred embodiment of the fiber optic sensor includes a housing 180. The housing may be constructed such that the housing seals the sensor interior from the external environment in order to exclude dust or other contaminants from the space between the fiber optic probe and the reflective surface of the material to be measured, or where desired depending upon the application, to create a partial or total vacuum that serves to control for the variable permittivity of the atmospheric free space (usually, air) between the conductors and thereby further improve the accuracy of the sensor. However, the use of a housing is not required. In yet another embodiment, the fiber probe may contain a single transmit fiber and a single receive fiber. However, any combination of fibers may be used to form the probe.

Figure 2:
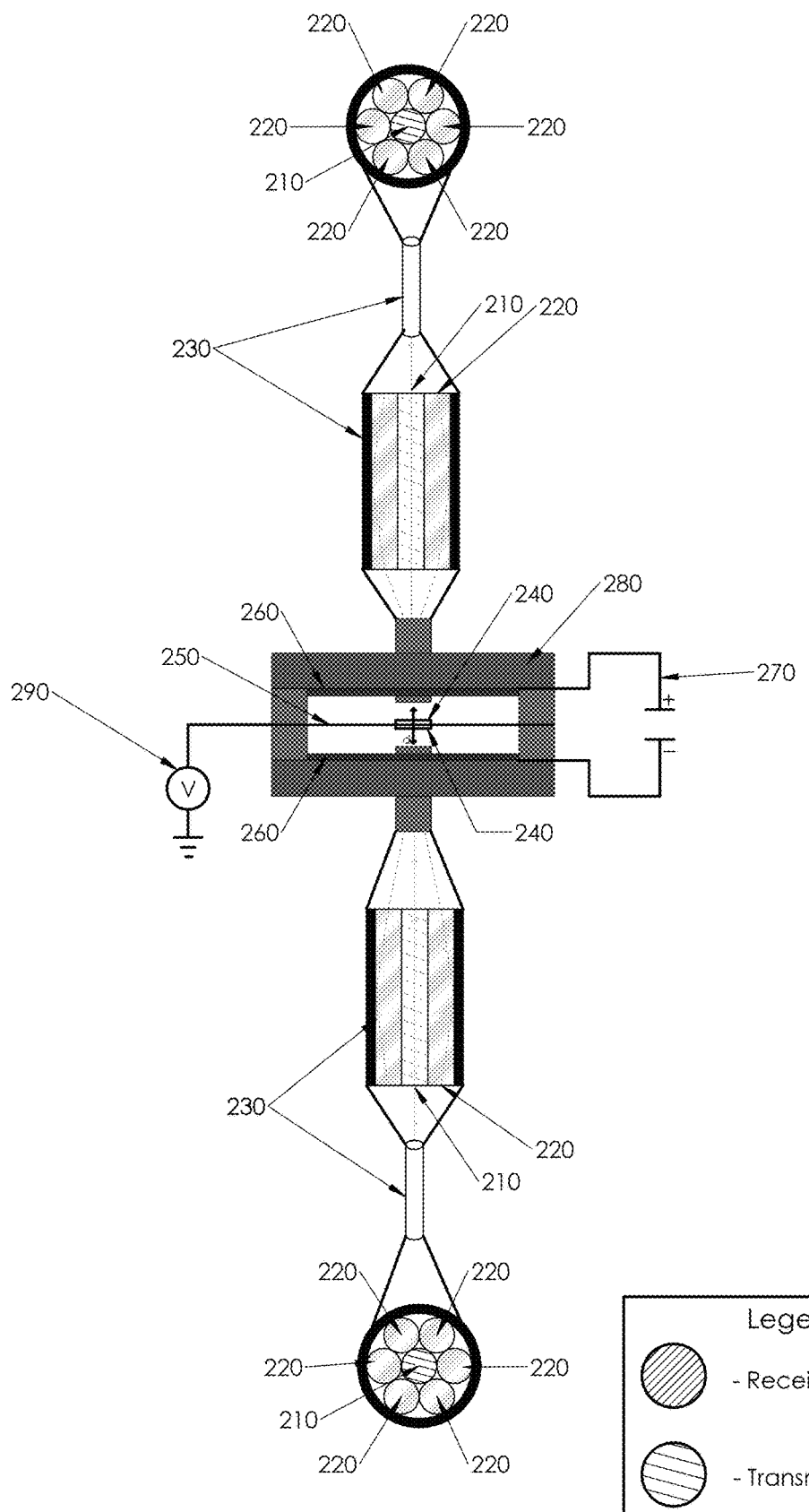
FIG. 2 shows an embodiment of a fiber optic electromagnetic phenomena sensor, configured to measure voltage or electric fields utilizing two optical probes.

FIG. 2 shows an embodiment of a fiber optic sensor identical in structure and operation as the structure as described above, but with an additional fiber probe element to allow for an additional measurement of the displacement caused by the introduced voltage. Here, an additional fiber bundle 230 featuring a transmitting fiber 210 having a first and second ends is placed adjacent to the reflective surfaces 240 of the third conductor element 250. As in FIG. 1, the conductive element 250 and the reflective surface 240 can be part of the same material (e.g.: a polished metal) or can be separate materials (such as a reflective coating). The first end of the transmitting fiber has a polished finish and the second end is coupled to a light source (not shown). The fiber bundle also features a multitude of receiving fibers 220 disposed around the transmitting fiber with each receiving fiber having first and second ends where the first ends are also polished and the second ends are coupled to a light detecting means (not shown). The fiber bundle is disposed within a tubing 230 such that the first end of the transmitting fiber and the first end of each receiving fiber is perpendicular and adjacent to the reflective side of the material 240 to be measured that exhibits a physical displacement when carrying a voltage and placed within a static electric field, with space between the fiber ends and the reflective side of the material. The two fiber bundles, coupled to the sensor electronics, take measurements of the opposite effects of the displacement in the third conductor element, allowing for a comparison of the displacement measurements in response to voltage and, as discussed further below, for correction of temperature dependencies, yielding a highly accurate measurement of voltage in either direct current or alternating current applications.

Figure 3:
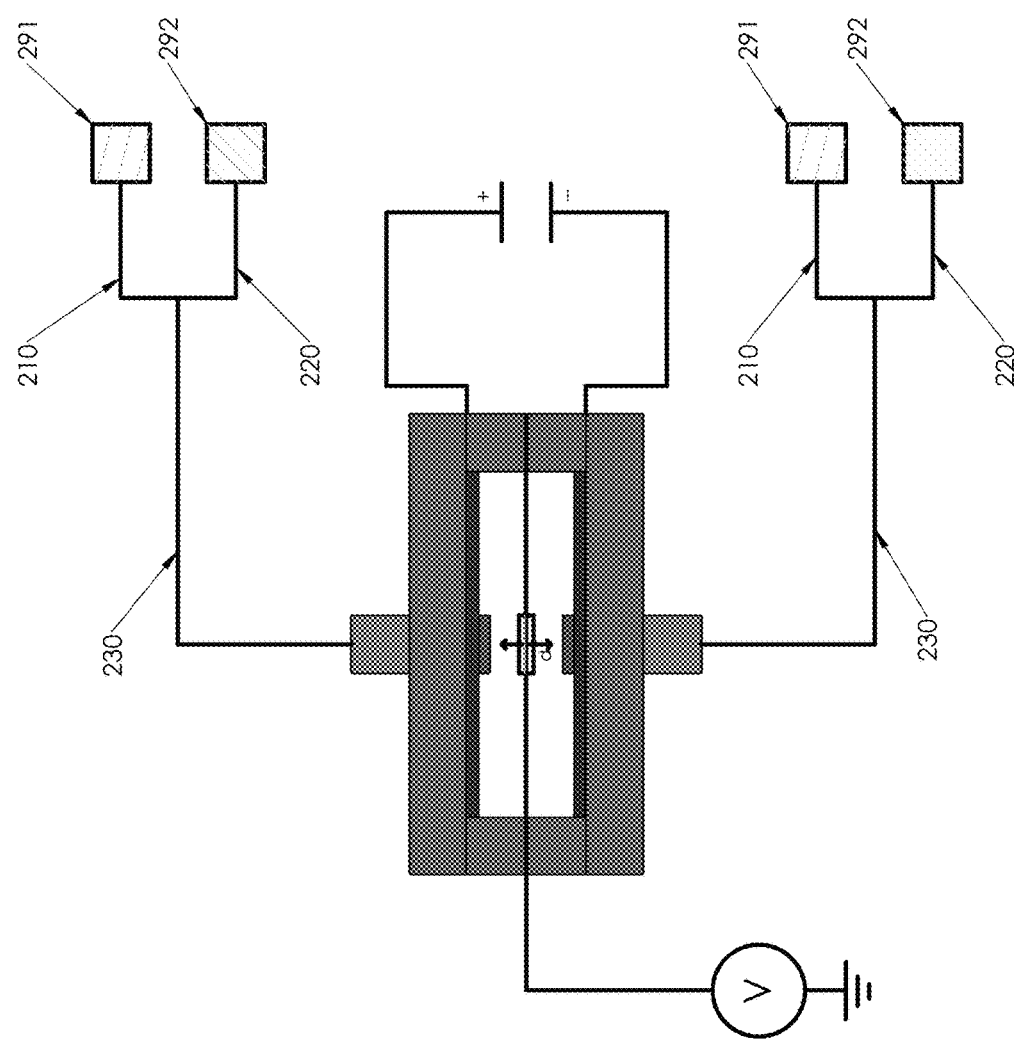
FIG. 3 shows an alternative view of the sensor embodiment depicted in FIG. 2, including the sensor's associated electronics.

FIG. 3 depicts the same fiber optic electromagnetic phenomena sensor as FIG. 2, but further depicts the electronic components of the sensor: the light source 291, here an LED, and the light detecting means 292, here a silicon PIN diode. The transmitting fiber 210 and the receiving fiber 220 of the fiber bundle 230 is coupled to the light source 291 and light detecting means 292 respectively.

The use of two optical probes to measure the displacement of the conductive element 250 (which changes the distance between the reflective surface of that element 240 and the fiber bundle 230) between the charged conductor plates 160 allows for compensation of temperature dependency issues that may introduce measurement error into measurements of DC power systems using optical sensing approaches. In AC systems, temperature dependency is less of an issue since the initial calibration of the probe to reflector distance is set at a given distance (for example, between 180 and 250 μm for this embodiment), and any subsequent expansion or contraction of the sensor element does not introduce substantial error into the measurement of an alternating current. However, in DC systems, the expansion and contractions in the sensor element materials due to temperature changes introduces measurement error into the sensor output which requires compensation. The disclosed sensor provides for accurate measurement in both AC and DC applications by taking multiple measurements of the displacement phenomena and using the multiple signals to isolate for both the signal of interest and temperature.

The use of two optical probes which allows for the correction of temperature dependencies can be more fully described as follows: In a direct current voltage measurement, the optical probe will measure the displacement, but that displacement will include a signal indicative of voltage as well as a signal indicative of temperature (i.e.: the thermal expansion of the sensor's conductor element and housing in reaction to changes in temperature). By using two optical probes, but positioning the second probe in a manner such that it measures the negative of the same effect, the signal of interest (voltage) can be readily separated from that of temperature by comparing the signal outputs from each probe.

To illustrate, Probe 1 detects a displacement signal (X1) which is comprised of a both a temperature signal (T1) and a voltage signal of interest (V1), and Probe 2 detects a displacement signal (X2), also comprised of a temperature signal (T2) and the voltage signal of interest (V2). Since the temperature effect of the element is common (i.e.: T1=T2), and the probes are arranged so that the probes take opposite measurements of the displacement (i.e.: X1=−X2), then the signals received from the two probes can be mathematically manipulated such that the temperature signal can be isolated from the signal of interest, here voltage (X1−X2=V1+V2) and determine the total temperature effect (X1+X2=T1+T2). In this manner, direct current measurements can be corrected for temperature effects. In addition, the use of this approach has the added advantage of addition of temperature sensor functionality. This netting of thermal expansion signals to correct for temperature effects upon measurement can be performed through the use of a hardware integration, such as a differential amplifier, or using a software integration, wherein the measurement outputs are netted mathematically to arrive at the same result.

To ensure maximum accuracy, the construction of the dual probe sensor should be such that the sensor performance is as close to identical as possible in performance, which can be achieved by ensuring that the fixed conductor elements are parallel to one another, that the third dynamic conductor element bisects the fixed conductors, that the optical fiber bundle and the opposite fiber bundle are substantially similar in their operating characteristics, such as the probe-reflector distance, the fibers' optical transmission performance, and the length of the fiber between the probe and the light source and light detector.

It will be appreciated that, using the multiple probe approach described above allows for the correction of temperature dependency challenges that are associated, in particular, with the optical measurement of direct current outputs and applies equally to measurements of voltage, current, electric and magnetic fields, and other electromagnetic phenomena in such systems. For example, a similar approach could be used to measure direct current or magnetic fields using other kinds of fiber optic electromagnetic phenomena sensors, such as those disclosed in the Electromagnetic Phenomena Sensor Patent Application.

Although this invention has been described in relation to the exemplary embodiments, it is well understood by those skilled in the art that other variations and modifications can be effected on the preferred embodiments without departing from the scope and spirit of the invention as set forth herein.

The invention claimed is:

1. A fiber optic sensor for measuring electric voltage, comprising:
   an optical fiber probe including at least one transmitting fiber having one end coupled to a light source and at least one receiving fiber having one end coupled to a light sensing means;
   two conductive elements arranged in parallel, such that upon being coupled to a voltage source an electric field is created between the two conductive elements;
   a conductive material having a reflective surface or a reflective body attached thereto, the conductive material bisecting the two conductive elements;
   the fiber probe being positioned such that the uncoupled ends of the fibers are adjacent to the reflective surface with space between the fibers and the reflective surface;
   wherein, light transmitted through the transmitting fiber emerges at the uncoupled end, propagates a short distance, and is reflected by the reflective surface into the at least one receiving fiber, and is detected by a light sensing means, with the conductive material arranged such that a physical displacement in the conductive material in response to the voltage to be measured causes a change in the distance between the fiber ends and the reflective surface, and the change in the distance modulates the amount of light reflected into the at least one receiving fiber.

2. The sensor in claim 1, further comprising:
   a second optical fiber probe including at least one transmitting fiber having one end coupled to a light source and at least one receiving fiber having one end coupled to a light sensing means;
   the conductive material being reflective on at least two sides or having a second reflective surface or a reflective body attached thereto;
   the second fiber probe being positioned such that the uncoupled end of the fibers are adjacent to the second reflective surface of the conductive material with space between the fibers and the reflective surface.

3. The sensor in claim 1, wherein the sensor measures current with a frequency below 70 Hz.

4. The sensor in claim 1, wherein the physical displacement of the conductive material is caused by the force explained by Coulomb's Law.

5. The sensor in claim 1, where the conductive material is a conductive wire or strip.

6. The sensor in claim 1, wherein the conductive material has a reflective layer or coating to enhance its light reflective properties.

7. The sensor in claim 1, further including a housing enclosing the uncoupled end of the fiber optic probe, the conductive material, the reflective surface of the conductive material; and the two conductive elements arranged in parallel.

8. The sensor in claim 7, wherein the housing is sealed from exterior contamination.

9. The sensor in claim 7, wherein the housing comprises means to set the distance between the fiber probe and the reflective surface of the conductive material.

10. The sensor in claim 1, wherein the light source is a light emitting diode or a laser.

11. The sensor in claim 1, wherein in the light sensing means is at least one of a PIN detector, a photodiode, a photomultiplier tube, or a semiconductor-metal detector.

12. The sensor in claim 1, wherein the distance between the fiber probe and the reflective surface of the conductive material is in a range of 0 to 500 microns.

13. The sensor of claim 1, wherein a plurality of receiving fibers are used.

14. The sensor of claim 1, wherein the at least one receiving fibers consist of six fibers arranged surrounding the transmitting fiber.

15. The sensor in claim 2, wherein the sensor takes measurements of the displacement in the conductive material in at least two directions, allowing for a comparison of the displacement measurements in response to voltage.

16. The sensor in claim 15, wherein the output measurements of the two fiber probes are compared in order to correct for sensor temperature dependency.

17. The sensor in claim 2, wherein the sensor measures current with a frequency below 70 Hz.

18. The sensor in claim 2, wherein the physical displacement of the conductive material is caused by the force explained by Coulomb's Law.

19. The sensor in claim 2, where the conductive material is a conductive wire or strip.

20. The sensor in claim 2, wherein the conductive material has at least one reflective layer or coating to enhance its light reflective properties.

21. The sensor in claim 2, further including a housing enclosing the uncoupled end of the fiber optic probe, the conductive material, the reflective surface of the conductive material, and the two conductive elements arranged in parallel.

22. The sensor in claim 21, wherein the housing is sealed from exterior contamination.

23. The sensor in claim 21, wherein the housing comprises means to set the distance between the fiber probe and the reflective surface of the conductive material.

24. The sensor in claim 2, wherein the light source is a light emitting diode or a laser.

25. The sensor in claim 2, wherein in the light sensing means is at least one of a PIN detector, a photodiode, a photomultiplier tube, or a semiconductor-metal detector.

26. The sensor in claim 2, wherein the distance between the fiber probe and the reflective surface of the conductive material is in a range of 0 to 500 microns.

27. The sensor of claim 2, wherein a plurality of receiving fibers are used.

28. The sensor of claim 2, wherein the at least one receiving fibers consist of six fibers arranged surrounding the transmitting fiber.

29. A system of intensity modulated fiber optic sensors for detecting voltage, comprising:
- at least one intensity modulated fiber optic voltage sensor;
- at least one light source;
- at least one light sensing element for each sensor;
- at least one optical fiber arranged to transmit light from the light source to each fiber optic sensor;
- at least one optical fiber arranged to transmit light from each fiber optic sensor to its light sensing element; and
- a converter that receives the electrical signal outputs from the light sensing elements and converts the electrical signals into a digital output of the measured voltage, with the system taking at least one measurement of voltage with a frequency of lower than 10 Hz;
- and a processor that compares the output difference between the signals generated by each light sensing element.

30. The system according to claim 29, wherein the system is capable of measuring voltage in both alternating current (AC) and direct current (DC) systems.

31. The system according to claim 29, wherein the fiber optic sensors measure voltage present in equipment used in the generation, transmission, and distribution of electrical power.

32. The system according to claim 31, wherein the equipment is located within an electrical substation or is located on a distribution feeder.

* * * * *